(12) United States Patent
Atwood et al.

(10) Patent No.: US 7,132,571 B2
(45) Date of Patent: Nov. 7, 2006

(54) SELF-ASSEMBLED CALIXARENE-BASED GUEST-HOST ASSEMBLIES FOR GUEST STORAGE BY VAN DER WAALS CONFINEMENT

(75) Inventors: Jerry L. Atwood, Columbia, MO (US); Leonard J. Barbour, Columbia, MO (US); Agoston Jerga, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 10/141,733

(22) Filed: May 9, 2002

(65) Prior Publication Data

US 2003/0212301 A1 Nov. 13, 2003

(51) Int. Cl.
*C07C 211/00* (2006.01)

(52) U.S. Cl. .................. 564/308; 564/306; 564/307
(58) Field of Classification Search ............... 564/305, 564/306, 307; 568/300, 367, 376
See application file for complete search history.

(56) References Cited

U.S. PATENT DOCUMENTS 6,342,634 B1    1/2002   Nicholson et al.

OTHER PUBLICATIONS

MacGillivray et al., A. chiral spherical molecular assembly held together by 60 hydrogen bonds, Nature, 389, 469–472.*

\* cited by examiner

*Primary Examiner*—Johann Richter
*Assistant Examiner*—Karl Puttlitz
(74) *Attorney, Agent, or Firm*—William D. Jackson

(57) ABSTRACT

A guest-host assembly having a generally spheroidal host assembly formed of trimers of calixarene molecules in a hexagonal close-packed assembly and its preparation. The calixarene trimers are associated together predominantly by van der Waals forces to provide dilated channels having void volumes within the range of 100–200 $Å^3$. A guest component, such as hydrogen, methane, or another hydrocarbon or halocarbon, is encapsulated within the dilated channels of the spheroidal host assembly and retained within the channels primarily by van der Waals forces. The guest-host assembly is stable at a temperature of 150° C. or higher. The temperature at which the onset of the release of the guest component occurs is within the range of 150–300° C.

12 Claims, 2 Drawing Sheets

SELF-ASSEMBLED CALIXARENE-BASED GUEST-HOST ASSEMBLIES FOR GUEST STORAGE BY VAN DER WAALS CONFINEMENT

FIELD OF THE INVENTION

This invention relates to generally spheroidal host assemblies formed of trimers of calixarene molecules and the preparation of such assemblies and their use in confining guest components through van der Waals forces.

BACKGROUND OF THE INVENTION

Various calixarene-type compounds and self-assembled and spherical hexamers of calixarene derivatives have been proposed for various applications. For example, MacGillivray and Atwood in a paper entitled "A Chiral Spherical Molecular Assembly Held Together by 60 Hydrogen Bonds," Nature, Vol. 389, pp. 469–472, October 1997, disclose a self-assembly mechanism for methylcalix[4]resorcinarenes self-assembled as a spherical hexamer along with adventitious water molecules. MacGillivray et al disclose the use of methylene-bridged resorcinarenes to form hexameric superstructures. MacGillivray makes reference to exploring various applications including a chiral catalyst for chemical transformations, a micro-vesicle for drug delivery, and an intermediate for separation problems.

Subsequent to the MacGillivray/Atwood paper, Gerkensmeier et al in a paper entitled "Self-Assembly of 2,8,14,20-Tetraisobutyl-5,11,17,23-tetrahydroxyresorc[4]arene," European Journal of Organic Chemistry, 1999, pp. 2257–2262, discuss self-assembling systems based upon hydroxyresorcinarenes generated by the acid catalyzed condensation of 2-hydroxyresorcinol (pyrogallol) with aldehydes in polar media. Here, the self-assembly products were characterized as two-dimensional polymeric structures held together by hydrogen bonds. The Gerkensmeier et al paper does, however, report on the preparation of a spherical hexamer having an enclosed interior space populated by ten solvent molecules. However, attempts to replicate this hexamer structure were unsuccessful, and the structure was characterized by Gerkensmeier et al as being very fragile due to its being stabilized by weak hydrogen bonds.

The self-assembled host structures arrived-at through procedures, such as described in MacGillivray/Atwood and Gerkensmeier et al papers, are in the form of molecular structures which are maintained through chemical bonding such as covalent bonding or hydrogen bonding. Thus, as described in the MacGillivray/Atwood paper, the calixarene-based hexamers are sustained through intermolecular bonding formed predominantly through hydrogen bonds involving the adventitious water molecules.

SUMMARY OF THE INVENTION

In accordance with the present invention, there is provided a composition of matter comprising a guest-host assembly having a generally spheroidal host assembly formed of trimers of calixarene molecules in a hexagonal close-packed assembly. The calixarene trimers are associated together predominantly by van der Waals forces to provide dilated channels having void volumes within the range of 100–200 Å$^3$. A guest component is encapsulated within the restricted channels of the spheroidal host assembly and retained within the channels primarily by van der Waals forces. The guest-host assembly is stable at a temperature of 150° C. (or higher). Preferably, the guest-host assembly is stable under conditions to provide a temperature at which the onset of the release of the guest component occurs within the range of 150–300° C.

In a preferred embodiment of the invention, the guest component is selected from the group consisting of hydrogen, methane, and hydrocarbons having molecular weight within the range of 2–520.

In a further embodiment of the invention, there is provided a method of forming a guest-host assembly which can be employed to release a guest component for a suitable use, such as for a fuel and a utilization process. In carrying out this embodiment of the invention, there is provided a generally spheroidal assembly formed of trimers of calixarene molecules in a hexagonal close-packed assembly of the trimers associated together predominantly by van der Waals forces. The assembly provides dilated channels having void volumes within the range of 100–200 Å$^3$. A guest component is infused into the dilated channels of the host assembly to provide a guest-host assembly in which the guest component is retained in the assembly predominantly by van der Waals forces. Preferably, the guest-host assembly of the infused guest component is stable at a temperature of at least 150° C. When it is desired to utilize the guest component, the guest-host assembly is heated to a temperature sufficient to destabilize the guest-host assembly and release the guest molecules. Preferably, the onset temperature of the release of the guest component is at least 150° C. and preferably within the range of 150–300° C.

The host assembly of molecules can then be reutilized by cooling the host assembly molecules and reassembling them to form a generally spheroidal assembly formed of trimers of the calixarene molecules in a hexagonal close-packed assembly associated predominantly by van der Waals forces to provide dilated channels having void volumes within the range of 100–200 Å$^3$. A guest component can then again be infused into the dilated channels of the guest-host assembly to provide a guest-host assembly in which the guest component is retained in the assembly predominantly by van der Waals forces and is stable to a temperature of at least 150° C.

DETAILED DESCRIPTION OF THE INVENTION

Figure 1:
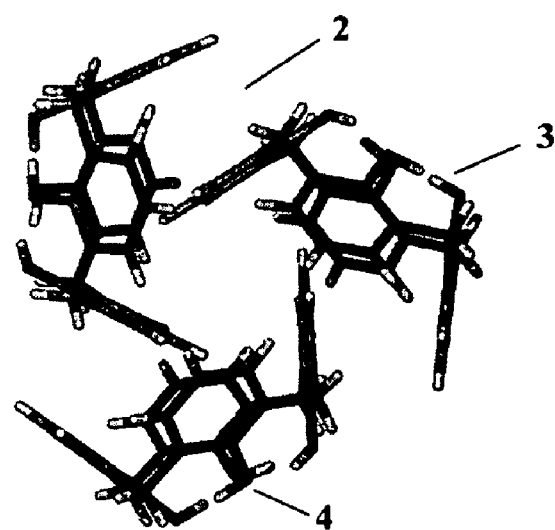
FIG. 1 is a schematic illustration of three calixarene molecules in a trimer arrangement.

The present invention involves an organic supramolecular framework that contains large, unoccupied lattice voids which are stabilized predominately by van der Waals interactions. The lattice voids of these framework systems are utilized to entrap and retain highly volatile gases. This can be accomplished indefinitely at high temperatures even under vacuum. The supramolecular assemblies involved in the present invention are based upon assemblies of calixarenes or derivatives of calixarenes. The preferred application of the invention involves the use of calix[4]arene; however, other calixarenes, such as calix[6]arene and calix

[8]arene, can be employed in carrying out the invention. Derivatives of such calixarenes can be employed to achieve the closely-packed spheroidal assemblies involved in the present invention. However, contrary to functionalized calixarenes, such as resorcinarenes, the calixarenes employed in the present invention are assembled predominantly by van der Waals forces as opposed to strong chemical bonding, such as may be achieved through the use of functional substituents on the aromatic nuclei. The invention will be described in detail with regard to the use of calix[4]arene to form hexagonal close-packed assemblies for the inclusion of low molecular weight guest moieties.

The calixarenes comprise an extensively studied class of macrocyclic polyphenolic compounds that are usually strongly associated with host/guest inclusion chemistry. The simplest representative of this family of compounds is calix[4]arene, which forms from four methylene-bridged phenyl groups, as indicated by the following structural formula:

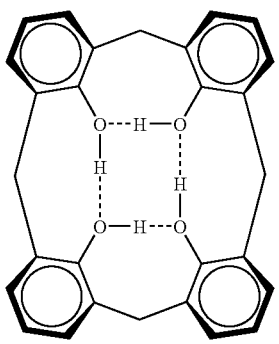

(1)

Calix[4]arene provides a bowl-shaped molecule with a shallow cleft and a rigid cone conformation which is stabilized by a cyclic array of hydrogen bonds between adjacent phenolic OH groups at the lower rim. As indicated by the experimental work described below respecting calix[4]arene, its crystalline inclusion compounds exhibit particularly unusual structural characteristics, in addition to extraordinary thermal stability.

While the calixarene compounds employed in carrying out the present invention will normally be fully aromatized, as indicated by the Structure (1), one or more of the aryl groups may be hydrogenated. For example, a calixarene suitable for use in carrying out the present invention would include cyclohexylcalixarene in which one aromatic group has been hydrogenated to form a cyclohexyl group, as indicated by the following structural formula.

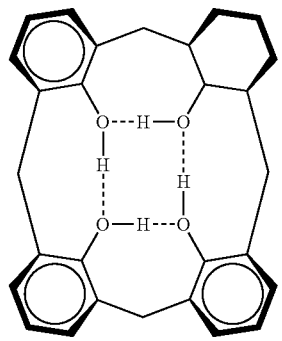

(2)

In addition, the bridge groups formed by the methylene bridges can be replaced by other bridged structures which are sterically similar to the methylene bridges. For example, sulfur bridges can be provided in lieu of the carbon bridges, as indicated by the thiacalixarene shown by the following structural formula.

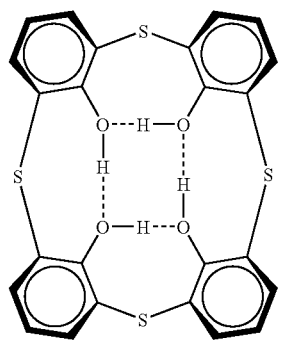

(3)

Other suitable bridging agents would include silanyl groups in which the methylene groups are replaced with silanyl, —SiH$_2$—. As will be recognized by those skilled in the art, such calixarene derivatives bear a very close stearic configuration to the normally encountered calixarenes. Such compounds may also incorporate hydrogenated aromatic groups, similarly as shown by the cyclohexyl-calix[4]arene of Formula (2).

The embodiment of the invention carried out involving calix[4]arene will be described with reference to the fully aromatized methylene-bridged calix[4]arene depicted by Formula (1). However, it will be recognized that such description is also applicable to the use of calix[4]arene involving hydrogenated aryl groups, as depicted by Formula (2), or by calix[4]arenes formed with bridges other than methylene bridges, such as depicted by Formula (3).

Calix[4]arene is soluble in a variety of aromatic and aliphatic solvents. The structure of an acetone solvate, resulting from evaporation of a solution of calix[4]arene in acetone, is characterized as a 1:1 host/guest complex with each acetone guest molecule inserting one of its methyl groups into a calixarene cavity. When exposed to air, the crystalline material decomposes readily as 2/3 of the acetone is released in vapor form, with concomitant rearrangement of the host lattice and the remaining acetone guest. Desolvation results in powdering of the crystals, and even mild heating at 50° C. accelerates the process considerably.

Diffraction-quality single crystals of pure calix[4]arene were grown by sublimation at 300° C. under reduced pressure (2 torr), and the guest-free structure was elucidated. Comparison of the calculated powder diffraction (XRD) pattern of the sublimed phase with that obtained experimentally for the 2/3 desolvated acetone phase confirms that the two structures are isomorphous. Pure calix[4]arene crystallizes in the hexagonal space group P6$_3$/m: As shown in the schematic three-dimensional representation of FIG. 1, three calixarene molecules, 2, 3, and 4, adopt a cyclic, mutually included arrangement in the form of a trimer. The trimer thus formed is approximately spherical in shape and the extended structure is a hexagonal close-packed assembly of trimers. No intermolecular hydrogen bonds are present in the structure and the trimer appears to be held together predominantly, and perhaps solely, by the relatively weak van der Waals interactions.

Figure 2:
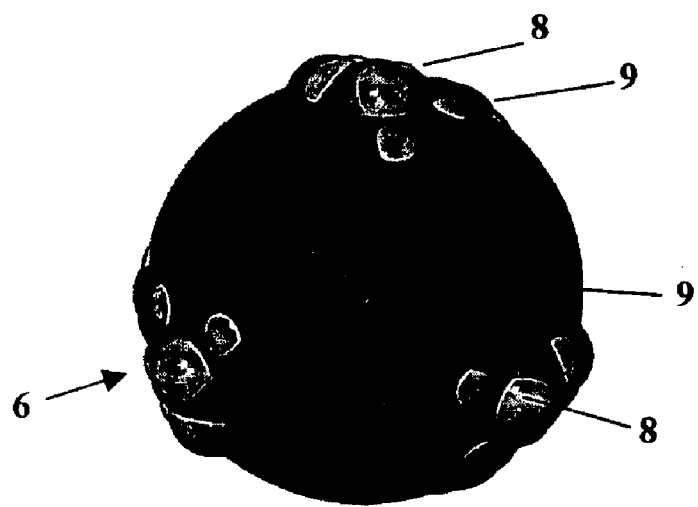
FIG. 2 is a space-filling representation of the cyclic trimer viewed along a threefold axis.

FIG. 2 illustrates a space-filling representation of the cyclic trimer of calix[4]arene illustrated schematically in FIG. 1. Here, the space-filling representation is viewed along the threefold axis. The generally spherical configuration illustrated by reference numeral 6 has a radius of about 7.3 Å. The calix[4]arene moieties are indicated generally by carbon atoms indicated by spheres 8 and hydrogen atoms indicated generally by lightly colored smaller spheres indicated by reference numeral 9.

Figure 3:
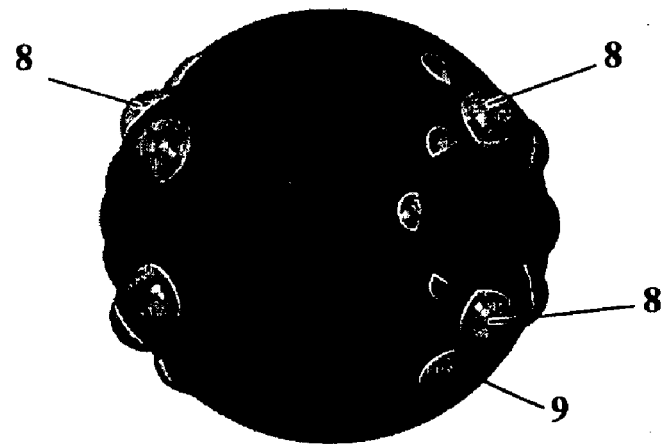
FIG. 3 is a representation of the cyclic trimer of FIG. 2 viewed perpendicular to the axis of FIG. 2.

FIG. 3 illustrates a space-filling representation of the cyclic trimeric arrangement of calixarenes viewed perpendicular to the threefold axis. Carbon and hydrogen atoms are gain indicated generally by the spheroids 8 and 9, respectively An ideal hexagonal close-packed (hcp) lattice of spherical entities contains a three-dimensional network of parallel and oblique channels (with respect to the crystallographic c axis) that link interstitial voids. Two types of channels that run parallel to [001] can be identified. One type of channels, characterized as type a channels, are continuous and link voids that are bounded by a trigonal antiprismatic arrangement of six spheres. Another type of channels, type b channels, is not continuous and is surrounded by five spheres in a trigonal bipyramidal environment. The structure of the hexagonal close-packed assembly of this invention deviates from ideal spherical geometry such that minor protrusions and indentations manifest themselves, as shown in FIGS. 2 and 3. These undulations result in substantial dilation of the b channels to yield "solvent accessible" voids of about 153 Å$^3$. Furthermore, constriction of the oblique and type a channels ensures that the bulk structure is non-porous. The hexagonal close-packed (hcp) assembly arrangement of trimers, as described above, also obtains in the dichloromethane, chloroform, and acetonitrile solvates. In all three cases, the guest is situated in the interstitial void and is intricately disordered as a result of its loose fit and the presence of high crystallographic site symmetry.

In order to probe the cavity size, crystals of the CCl$_4$ solvate were prepared by slow evaporation of a solution of calix[4]arene in CCl$_4$. Again we observe the hexagonal close-packed host framework, but in this case the more symmetrical CCl4 solvent is not disordered and therefore easily modeled. The guest is trapped in the interstitial lattice cavity and makes only van der Waals contact with the host. An investigation was undertaken of the thermal stability of the hexagonal close-packed assembly inclusion compounds of calix[4]arene relative to that of its pure phase. Thermogravimetric analysis (TGA) of the CCl$_4$ solvate shows that the inclusion compound is stable up to 200° C. This temperature marks the onset temperature of guest release ($T_{on}$) (the weight loss recorded between 200 and 250° C. corresponds to a 1:1 complex of trimers and CCl$_4$).

The parameter ($T_{on}-T_b$) has been shown to be a reliable measure of the relative thermal stability of host-guest systems, where $T_b$ is the normal boiling point of the guest. The thermal stability of the hexagonal close-packed host lattice is remarkably high, despite the presence of a relatively volatile guest ($T_{on}-T_b$ for trimers·CCl$_4$=120° C.). In view of these findings, experimental work was undertaken to assess the ability of the host lattice to stabilize increasingly volatile guests that are structurally related to CCl$_4$. The possibility thus presents itself of entrapping a range of highly volatile freon and halon compounds in the interstitial cavity which results from the hexagonal close-packed assembly. Several such host-guest compounds were prepared as single crystals, and pertinent parameters are given in Table 1. All of these crystals exhibited remarkable thermal stability as determined by TGA.

Inclusion compounds of calix[4]arene with selected guest compounds, guest boiling points (b.p.) and hexagonal unit cell parameters.

TABLE 1

Inclusion compounds of calix[4]arene with selected guest compounds, guest boiling points (b.p.) and hexagonal unit cell parameters.

| No. | Complex host | guest b.p./° C. | a/Å | c/Å |
| --- | --- | --- | --- | --- |
| — | † | — | 14.344 | 18.627 |
| 3 | 1.CCl$_4$ | 76.8 | 14.592 | 18.386 |
| 4 | 1.CHCl$_3$ | 61.2 | 14.697 | 17.953 |
| 5 | 1.CH$_2$Cl$_2$ | 39.8 | 14.69 | 17.99 |
| 6 | 1.CFCl$_3$ | 23.7 | 14.636 | 18.245 |
| 7 | 1.CF$_2$ClBr | −4 | 14.643 | 18.235 |
| 8 | 1.CF$_3$CH$_2$F | −15 | 14.640 | 18.220 |
| 9 | 1.CF$_3$Br | −57.7 | 14.487 | 18.227 |
| 10 | 1.C$_2$F$_6$ | −78.2 | 14.647 | 18.195 |
| 11 | 1.CF$_4$ | −127.9 | 14.615 | 18.284 |
| 12 | 1.(CH$_4$)$_2$ | −160 | 14.599 | 18.283 |

†Guest-free calix[4]arene trimer formed from pure calix[4]arene obtained by sublimation at 300° C. under vacuum.

Figure 4:
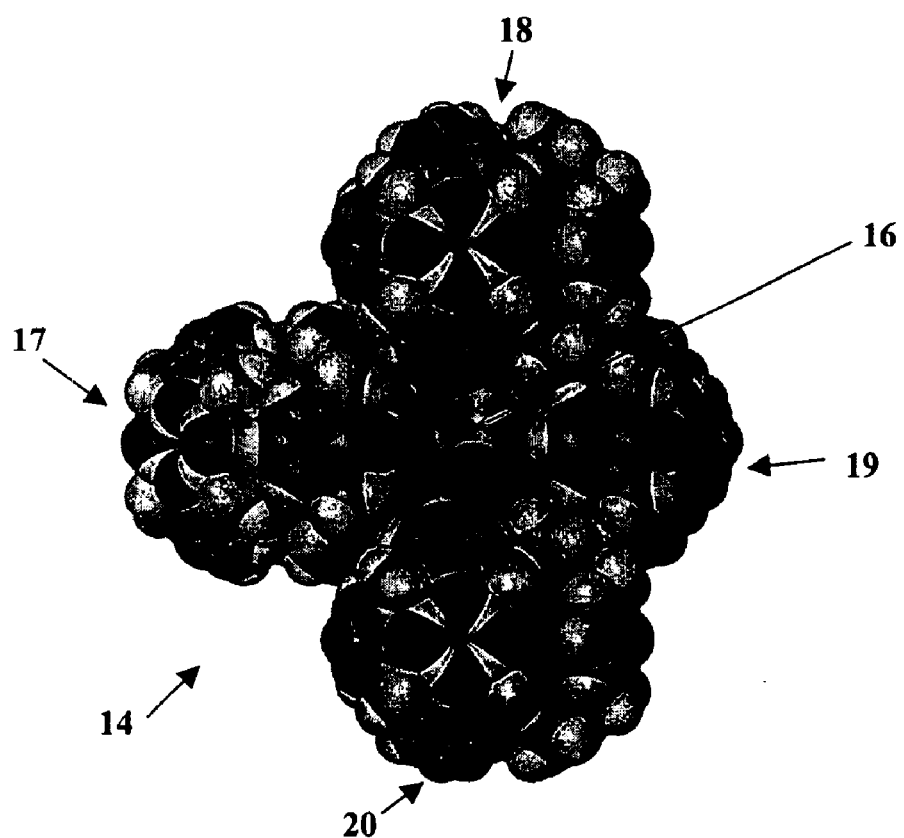
FIG. 4 is a space-filling representation of a spheroidal guest-host assembly.

The very low solubility of calix[4]arene in condensed volatile freons such as CF$_3$Br, C$_2$F$_6$ and CF$_4$ precludes the growth of diffraction quality crystals after the procedure used to obtain the trimer·CCl$_4$ assembly (1.CCl$_4$). However, solvent-free hexagonal close-packed assembly crystals can be precipitated by the addition of propan-2-ol to a solution of calix[4]arene in tolune. A modification of this method involving dissolution of a condensed freon or halon of interest in the toluene can be employed to obtain diffraction-quality single crystals within 30 min. In some cases, satisfactory modeling of the guest within the hexagonal close-packed lattice was hampered by disorder and thermal motion. However, in all cases, microanalysis and solution $^{19}$F nuclear magnetic resonance (NMR) confirmed the presence of the halocarbon guest. Host-guest ratios were determined by means of TGA. In the case of the CF$_3$Br inclusion compound, the guest was simply disordered over two positions and easily modeled. CF$_3$Br, positioned in the interstitial cavity of the hexagonal close-packed assembly lattice, is shown in FIG. 4. FIG. 4 is a space-filling representation of a spheroidal guest-host assembly in which the host assembly is formed by five trimers of calix[4]arene with the interstitial void (type b channels) of the host lattice occupied by one molecule of CF₃Br, as indicated generally by reference numeral 16. In FIG. 4 one of the five units of the calix[4]arene trimer has been omitted in order to reveal the position of the CF₃Br guest within the cavity. The calix[4]arene trimers are indicated by reference numerals 17, 18, 19, and 20.

The dilated type b channels provided by the hexagonal close-packed host assemblies employed in the present invention provide void volumes within the range of 100–200 Å3. In preferred applications of the present invention involving relatively volatile guest components, the dilated channels will usually exhibit void volumes within the range of 140–170 cubic Angstroms and, more specifically, within the range of 150–160 Å3.

As described below embodiments of the present invention involve confinement of volatile hosts in replenishable vessels or containers. In consideration of applications involving gas confinement (e.g., size-selective separation and storage procedures), it might not be convenient to implement the technique of precipitation from a toluene solution in which the gas of interest is also dissolved. The hcp phase has the structural characteristics of an interstitial solid solution. While the host lattice does not require occupancy of the interstitial void in order to maintain its structural integrity, the presence of suitably sized guest species favors formation of an even more densely packed structure based upon an already stable host framework.

Since clathration involves a phase transformation of the host lattice in order for the guest to become lodged in the lattice voids, experimental work was carried out involving the previously observed desolvation of the metastable, non-hcp calix[4]arene acetone solvate. Large single crystals of the acetone 1:1 complex were grown, crushed, and placed in a steel pressure vessel. Freon gas was introduced into the vessel, which was then sealed and heated to 50° C. After approximately 12 hours, the crystals were removed and subjected to x-ray diffraction (XRD), NMR, TGA, and microanalysis, which together confirmed the hexagonal structure as well as the near-stoichiometric lattice inclusion of the freon gas. These results show that, in the presence of a suitable guest vapor, even a solid—solid phase transition of the host to the hexagonal close-packed lattice facilitates guest inclusion.

Further experimental work was carried out to entrap CH₄ at room temperature by exposure at 100 atm. for 72 hours. The resulting powder was dissolved in d⁶-benzene and analyzed by ¹H-NMR, which revealed the presence of methane. TGA analysis yielded a weight-loss of 2.43% with $T_{on}$ within the range of 150–170° C., corresponding to two methane molecules per lattice void. (The calculated CH₄ weight loss for 1.(CH₄)₂ is 2.45%.) Although single crystals containing methane could be obtained from toluene/propan-2-ol under a high pressure of methane, a reasonable model incorporating methane could not be elucidated because of guest disorder.

The thermal stability for the hexagonal close-packed inclusion compounds is indicated by the following values of $T_{on}$-$T_b$ for the guests CF₃Br (260° C.), CF₄ (370° C.), and .CH₄ (320° C). This remarkable thermal stability of the hexagonal close-packed assembly inclusion compounds is attributed to the host lattice being isomorphous with its pure phase; that is, the host lattice cannot gain much stability by releasing the guest because the initial and final lattices would be identical, even at elevated temperatures. In contrast to the zeolites, the guest cannot easily diffuse through the host lattice since the channels are non-porous.

A preferred application of the present invention is in the storage of volatile fuels, such as hydrogen and methane. Because of the high temperature stability of the calixarene-based host assemblies, they can advantageously be employed in fuel storage cells for vehicles powered by the combustion of hydrogen or methane as the fuel source. For example, the dilated type b channels as defined, the hexagonal close-packed assembly of calix[4]arenes as described above, are characterized as "dumbbell"-shaped voids with enlarged chambers at each end, interconnected by a reduced diameter channel extending between the chambers. For methane storage, two methane molecules may occupy a dilated channel, one molecule in each of the enlarged chambers. For hydrogen storage, hydrogen molecules may be retained within the end chambers as well as within the reduced diameter channel extending between the chambers. The guest hydrogen or methane molecules are retained within the hexagonal close-packed assembly of the calix[4]arenes predominantly by van der Waals forces as contrasted with strong chemical bonding.

In this embodiment of the invention, the fuel cell incorporating lattice structure of calixarene molecules in a hexagonal close-packed assembly can be used to retain a volatile fuel component, such as hydrogen, within the void spaces. The fuel cell can be heated by means of either direct or indirect heat exchange using the internal combustion engine, to which the hydrogen fuel is supplied. The hydrogen fuel released through destabilization of the guest-host assembly is then supplied to fuel the internal combustion engine. The fuel cell from which the hydrogen is supplied can be regenerated by cooling the host assembly molecules to reassemble them into the hexagonal close-packed assembly. The fuel cell can then be infused with hydrogen from a suitable source to reestablish the fuel cell in which the hydrogen fuel component is retained as a guest in the guest-host assembly predominantly by van der Waals forces.

As noted above, host assemblies incorporating calix[4]arene molecules are particularly preferred for fuel cells involving the storage of very low molecular weight volatile fuel components, specifically methane, ethane, and hydrogen, H₂. Propane and butane can also be stored in such host assemblies. Further, the invention may be utilized in forming fuel cells suitable for the storage of higher molecular weight but still volatile fuel components, such as propane and butane and higher molecular weight hydrocarbons. In this case, guest-host assemblies based upon somewhat higher molecular weight calixarenes, such as calix[6]arene and calix[8]arene, may be conveniently employed to provide somewhat larger dilated channels to entrap the higher molecular volatile fuels, such as butane and heavier hydrocarbons, as guest components.

Another application of the invention involves the operation of a replenishable canister for release and subsequent recovery of a volatile component in a consrained environment. For example, the canister can be employed to retain a halon, which is effective as a combustion suppressant. Such an application will involve vehicles, such as space vehicles and the like, having constrained environments which may be susceptible to combustion when a heated source of combustion or potential combustion occurs within the constrained environment. The vessel containing the halon as a guest in a host/guest assembly of calixarene embodying the present invention is heated in order to arrive at a temperature sufficient to destabilize the guest-host assembly and to release the halon or other volatile component. The released component is supplied to the utilization location, such as a source of combustion or potential combustion. The host assembly molecules are then cooled in order to reassemble the molecules to form a hexagonal close-packed assembly of calixarenes, which, as described previously, are associated together predominantly by van der Waals forces. All or part of the halon can be recovered within the enclosed environment by circulating the oxygen-containing atmosphere through a compressor and separator to recover the halon and reintroduce the halon into the canister.

As noted previously, various host/guest assemblies can be prepared using calix[4]arene and various guest components. The following examples illustrate the preparation of various calixarene-based crystals as including calixarene crystals having guest-free structures as well as calixarene inclusion complexes formed with various guest components.

EXAMPLE 1

Preparation of the Calix[4]arene Crystals of the Guest-free Hexagonal Structure (1)

Diffraction-quality single crystals of pure calix[4]arene were grown by sublimation. A quantity of 50 mg (0.12 mmol) of calix[4]arene was placed in a pressure test tube attached to a vacuum line. The sample was heated to 300° C. under vacuum of ca. 2 torr, and within 5–6 minutes crystals of the guest-free structure, suitable for X-ray analysis were grown.

X-ray data were collected at room temperature on a Bruker SMART CCD diffractometer. All non-hydrogen atoms of the host molecules were refined anisotropically. Hydrogen atoms were placed using standard geometric models and with their thermal parameters riding on those of their parent atoms. Hydroxyl hydrogen atoms were located in difference electron density maps and refined with nominal geometric restraints.

The guest-free structure crystallizes in the hexagonal space group $P6_3/m$. Three calixarene molecules adopt a cyclic, mutually included arrangement. The trimer thus formed is approximately spherical in shape and the extended structure is simply a hexagonal close packed (hcp) assembly. No intermolecular hydrogen bonds are present in the structure and the trimer appears to be held together only by the relatively weak forces characterized as van der Waals interactions.

EXAMPLE 2

Preparation of the Non-hcp Calix[4]arene Crystals of the Acetone 1:1 Complex (1a)

The complex was prepared by slow evaporation of acetone from a saturated solution of calix[4]arene at room temperature. The saturated solution was prepared by successive addition of the solid material, i.e.: calix[4]arene, into 50 mL acetone at reflux temperature (58° C. at 1 atm). Large crystals of the non-hcp 1:1 complex were grown within 2–3 hours by cooling of the saturated solution. The crystals were kept in the mother liquor for further experiments.

The already reported structure (Cambridge Structural Database, Refcode: DACLUO) itself is of limited interest and is adequately described as a 1:1 host:guest complex with each acetone guest molecule inserting one of its methyl groups into a calix[4]arene cavity.

Crystals of 1a are metastable and, when exposed to the atmosphere, crystals of 1a by TGA), with concomitant rearrangement of the host lattice and the remaining acetone guest. Desolvation results in powdering of the crystals, and even mild heating (50° C.) accelerates the process. The X-ray powder diffraction (XRD) pattern of the material formed during the phase change compared to that of the sublimed phase confirms that the two structures are isomorphous. This would indicate that the 2/3 desolvated powder possesses a hcp structure, as does the sublimed guest-free calix[4]arene.

EXAMPLE 3

Preparation and Examination of the Thermal Stability of the $CCl_4$ 1:1 Inclusion Complex with 1 (Where 1 is the hcp Structure)

100 mg (0.24 mmol) of calix[4]arene was dissolved in carbon tetrachloride and to facilitate the dissolution the mixture was heated to boiling. X-ray quality crystals were grown by slow evaporation of the solvent within 2 hrs. The crystals exhibit the hcp host framework, as confirmed by X-ray diffraction analysis, but in this case the more symmetrical $CCl_4$ guest is not disordered, and therefore easily modeled. The guest is trapped in the interstitial lattice cavity and makes only van der Waals contact with the host calix[4]arene trimers.

In order to test the thermal stability of the hcp inclusion compounds of 1 relative to that of its pure phase, thermogravimetric analysis (TGA) was performed. TGA of the $CCl_4$ guest-containing hcp shows that the inclusion compound is stable up to 200° C., the onset ($T_{on}$) of guest release. The weight loss recorded between 200 and 250° C. corresponds to a 1:1 complex of $CCl_4$, $1.CCl_4$. This is in sharp contrast to the decomposition of 1a described above where guest-release by the non-hcp structure occurs readily ($T_{on}$=50° C.).

EXAMPLE 4

Preparation of the CF3Br 1:1 Inclusion Complex with 1, Method A

A quantity of 100 mg (0.21 mmol) non-hcp acetone complex, 1a, was placed in a steel pressure vessel. $CF_3Br$ gas was introduced into the vessel, which was then sealed and heated to 50° C. After approximately 12 hrs, the crystals were removed and subjected to X-ray diffraction analysis, nuclear magnetic resonance analysis (NMR), TGA and microanalysis, which, together, confirmed the hexagonal structure as well as the near 1:1 stoichiometric lattice inclusion of the gas.

EXAMPLE 5

Preparation of the $CF_3Br$ 1:1 Inclusion Complex with 1, Method B

The very low solubility of calix[4]arene in condensed $CF_3Br$ precludes the growth of diffraction quality crystals from saturated solutions. However, it had been noted that solvent-free hcp crystals could be precipitated by the addition of propan-2-ol to a solution of 1 in toluene. A modification of this method involving dissolution of condensed $CF_3Br$ in toluene under pressure (1–2 atms) affords diffraction-quality single crystals within 30 minutes. The structure was elucidated and showed one molecule of $CF_3Br$ in the hcp lattice void. TGA analysis showed [$T_{on}$-$T_b$] for $1.CF_3Br$=260° C.

EXAMPLE 6

Preparation of the $CF_4$ 1:1 Inclusion Complex with 1, Method A

A quantity of 100 mg (0.21 mmol) non-hcp acetone solvate, 1a, was placed in a steel pressure vessel. $CF_4$ gas was introduced into the vessel, which was then sealed and heated to 50° C. After approximately 12 hrs, the crystals were removed and subjected to TGA that confirmed the almost stoichiometric amount of guest in 1.CF$_4$. TGA further confirmed [T$_{on}$–T$_b$] for 1.CF$_4$=370° C.

EXAMPLE 7

Preparation of the CF4 1:1 Inclusion Complex with 1, Method B

To 1.0 mL saturated solution of calix[4]arene was added a partial drop of propane-2-ol and the mixture was placed in a pressure vessel. CF$_4$ gas was introduced and within 2 hrs single crystals of 1.CF$_4$ were precipitated. The X-ray data were collected at room temperature on a Bruker SMART CCD diffractometer. The structure was solved and refined to prove the location and stoichiometry of the CF$_4$ guest.

EXAMPLE 8

Preparation of the CF$_2$BrCl 1:1 Inclusion Complex with 1, Method A

A quantity of 100 mg (0.21 mmol) non-hcp acetone solvate, 1a, was placed in a steel pressure vessel. CF$_2$BrCl gas was introduced into the vessel, which was then sealed and heated to 50° C. After approximately 12 hrs, the crystals were removed and subjected to TGA that confirmed the almost stoichiometric amount of guest in 1.CF$_2$BrCl.

EXAMPLE 9

Preparation of the CF$_2$BrCl 1:1 Inclusion Complex with 1, Method B

X-ray quality single crystals were grown by precipitation. To 1.0 ml saturated solution of calix[4]arene in toluene was added a drop of propane-2-ol, and the mixture was placed in a pressure vessel. CF$_2$BrCl gas (ca. 2 atm) was introduced and within 1 hr single crystals of 1.CF$_2$BrCl were precipitated. The structure was elucidated, but satisfactory modeling of the guest within the hcp lattice was hampered by disorder. Further NMR investigation unambiguously confirmed the presence of the CF$_2$BrCl and the near stoichiometric lattice inclusion of the gas was determined by TGA.

EXAMPLE 10

Preparation of the CFCl$_3$ 1:1 Inclusion Complex with 1, Method A

A quantity of 100 mg (0.24 mmol) pure calix[4]arene was mixed with liquid CFCl$_3$ (b.p. 25° C., ca. 2 atm) in a pressure test tube. The closed tube was heated to 100° C., at which temperature all the solid was dissolved in solvent. The homogeneous solution was cooled down and the precipitated crystals were subjected to X-ray diffraction analysis that confirmed the presence of the guest and thermogravimetric analysis showed that all the hcp lattice voids were occupied by guest molecules.

EXAMPLE 11

Preparation of the CF$_3$CH$_2$F 1:1 Inclusion Complex with 1 (The Inclusion Complex with Office Duster)

To 1.0 mL toluene was added enough calix[4]arene to produce a saturated solution. Then the mixture was heated to 100° C. to facilitate the dissolution of the solid material. The addition of the calix[4]arene and the heating-cooling cycle were repeated until the room temperature solution becomes saturated. To this solution one drop of condensed CF$_3$CH$_2$F (office duster, b.p. −15° C.) was added, and single crystals were grown within 15–20 minutes. The crystals were subjected to X-ray diffraction analysis that confirmed the presence of the guest and thermogravimetric analysis showed that all the hcp lattice voids were occupied by guest molecules.

EXAMPLE 12

Preparation of the CH$_4$ 2:1 Inclusion Complex with 1

A quantity of 500 mg (1.04 mmol) non-hcp calix[4]arene:acetone complex was placed in a pressure vessel, and then methane gas was introduced. The conversion of the metastable phase to the hexagonal structure takes 72 hrs at room temperature and 1500 psi (100 atm). The resulting powder was dissolved in d$^6$-benzene and analyzed by $^1$H NMR, which unequivocally revealed the presence of methane (0.15 ppm). TGA analysis yielded a weight-loss of 2.43% with T$_{on}$=150–170° C. ([T$_{on}$–T$_b$]=370° C.) corresponding to two methane molecules per lattice void (calculated CH$_4$ weight loss for 1.(CH$_4$)$_2$ =2.45%). Single crystals containing methane were obtained from toluene/propan-2-ol under a high pressure of methane, and methane was shown to be present as a disordered guest.

EXAMPLE 13

Preparation of the H$_2$ 10:1 Inclusion Complex with 1

Theoretical calculations show that there can be 9–10 hydrogen molecules per void in the above hexagonal crystal lattice. The methane protocol was carried out to encapsulate hydrogen in the solid. A quantity of 500 mg (1.04 mmol) non-hcp calix[4]arene:acetone complex was placed in a pressure vessel, and hydrogen gas was introduced. After 72 hrs, at 80 atm and room temperature, TGA analysis showed conversion to the H$_2$ inclusion complex with ca. (H$_2$)$_{10}$.1.

Having described specific embodiments of the present invention, it will be understood that modifications thereof may be suggested to those skilled in the art, and it is intended to cover all such modifications as fall within the scope of the appended claims.

What is claimed is:

1. A method of forming a guest-host assembly and releasing a guest component from said guest-host assembly, comprising:
    (a) providing a spheroidal guest-host assembly having a host component formed of trimers of calixarene molecules in a hexagonal close-packed assembly of said trimers associated together predominantly by van der Waals forces to provide at least one dilated channel having a void volume within the range of 100–200 Å$^3$ and having a guest component encapsulated within said at least one dilated channel of said spheroidal host assembly and retaining within said channel predominantly by van der Waals forces, said guest-host assembly being stable at a temperature of at least 150° C.;
    (b) heating said guest-host assembly to a temperature in excess of 150° C., which is sufficient to destabilize said guest-host assembly and release the guest molecules;
    (c) cooling said host assembly molecules and reassembling said molecules to form a generally spherical assembly formed of trimers of said calixarene molecules in a hexagonal close-packed assembly of said trimers associated together predominantly by van der Waals forces to provide at least one dilated channel having a void volume within the range of 100–200 Å$^3$; and (d) infusing a guest component in the dilated channel of said host assembly to provide a guest-host assembly in which said guest component is retained in said assembly predominantly by van der Waals forces and is stable at a temperature of at least 150° C.

2. The method of claim 1 wherein said guest/host assembly is stable at a temperature of at least 200° C.

3. The method of claim 2 wherein said calixarene molecules comprise calix[4]arene molecules.

4. The method of claim 3 wherein said guest component is selected from the group consisting of hydrogen, methane, and ethane.

5. A method of forming a guest-host assembly and releasing a guest component from said guest-host assembly, comprising:

(a) providing a generally spherical host assembly formed of trimers of calixarene molecules in a hexagonal close-packed assembly of said trimers associated together predominantly by van der Waals forces to provide at least one dilated channel having a void volume within the range of 100–200 Å$^3$;

(b) infusing a guest component into the dilated channel of said host assembly to provide a guest-host assembly in which said guest component is retained in said assembly predominantly by van der Waals forces and is stable at a temperature of at least 200° C.;

(c) heating said guest-host assembly to a temperature in excess of 200° C., which is sufficient to destabilize said guest-host assembly and release the molecules of said guest component;

(d) cooling said host assembly molecules and reassembling said molecules to form a generally spherical assembly formed of trimers of said calixarene molecules in a hexagonal close-packed assembly of said trimers associated together predominantly by van der Waals forces to provide at least one dilated channel having a void volume within the range of 100–200 Å$^3$; and (e) infusing a guest component in the dilated channel of said host assembly to provide a guest-host assembly in which said guest component is retained in said assembly predominantly by van der Waals forces and is stable at a temperature of at least 200° C.

6. The method of claim 5 wherein said calixarene molecules comprise calix[4]arene molecules.

7. The method of claim 6 wherein said guest/host assembly has a thermal stability, K, within the range of 70°–460° C., as defined by:

$$K = T_{on} - T_b$$

wherein $T_{on}$ is the onset temperature of guest release in ° C. and
$T_b$ is the boiling point of the guest component in ° C.

8. The method of claim 6 wherein said guest component is selected from the group consisting of hydrogen, methane, and ethane.

9. A method of forming a guest-host assembly and releasing a guest component from said guest-host assembly, comprising:

(a) providing a generally spherical host assembly formed of trimers of calix[4]arene molecules in a hexgonal close-packed assembly of said trimers associated together predominantly by van der Waals forces to provide at least one dilated channel having a void volume within the range of 100–200 Å$^3$;

(b) infusing a guest component into the dilated channel of said host assembly to provide a guest-host assembly in which said guest component is retained in said assembly predominantly by van der Waals forces and is stable at a temperature of at least 150° C.; and (c) heating said guest-host assembly to a temperature in excess of 150° C., which is above the boiling point of said guest component and is sufficient to destabilize said guest-host assembly and release the molecules of said guest component.

10. The method of claim 9 wherein said assembly of calix[4]arene molecules comprise dilated channels having void volumes within the range of 140–170 Å$^3$.

11. The method of claim 9 wherein said guest/host assembly is stable at a temperature in excess of 200° C.

12. The method of claim 9 wherein said guest component is selected from the group consisting of hydrogen, methane, and ethane.

* * * * *